(12) United States Patent
Barak et al.

(10) Patent No.: US 11,712,309 B2
(45) Date of Patent: Aug. 1, 2023

(54) MAGNETIC FLEXIBLE CATHETER TRACKING SYSTEM AND METHOD USING DIGITAL MAGNETOMETERS

(71) Applicant: Magnisity Ltd., Hod-HaSharon (IL)

(72) Inventors: Ron Barak, Tel-Aviv (IL); Ariel Birenbaum, RaAnana (IL); Benjamin Greenburg, Hod-HaSharon (IL)

(73) Assignee: Magnisity Ltd., Hod-HaSharon (IL)

( * ) Notice: Subject to any disclaimer, the term of this patent is extended or adjusted under 35 U.S.C. 154(b) by 0 days.

(21) Appl. No.: 17/681,789

(22) Filed: Feb. 27, 2022

(65) Prior Publication Data

US 2022/0175468 A1 Jun. 9, 2022

Related U.S. Application Data

(63) Continuation of application No. PCT/IL2020/050972, filed on Sep. 7, 2020.

(60) Provisional application No. 62/897,599, filed on Sep. 9, 2019.

(51) Int. Cl.
*A61B 34/20* (2016.01)
*A61B 5/06* (2006.01)

(52) U.S. Cl.
CPC .............. *A61B 34/20* (2016.02); *A61B 5/062* (2013.01); *A61B 2034/2072* (2016.02)

(58) Field of Classification Search
None
See application file for complete search history.

(56) References Cited

U.S. PATENT DOCUMENTS

| 4,710,708 A | 12/1987 | Rorden et al. |
| 5,307,072 A | 4/1994 | Jones, Jr. |
| 5,347,289 A | 9/1994 | Elhardt |

(Continued)

FOREIGN PATENT DOCUMENTS

| EP | 2849669 | 3/2015 |
| JP | 2011-059091 | 3/2011 |

(Continued)

OTHER PUBLICATIONS

International Preliminary Report on Patentability dated Jul. 1, 2021 From the International Bureau of WIPO Re. Application No. PCT/IL2019/051363. (8 Pages).

(Continued)

*Primary Examiner* — Bill Thomson
*Assistant Examiner* — Delia M. Appiah Mensah

(57) ABSTRACT

A method for magnetic tracking of a flexible catheter device or another flexible elongated device, the method comprising: receiving by a host server a plurality of sensed values of a local magnetic field, sensed by a respective plurality of sensors, wherein the host server is optionally included in a controller of the sensors, the sensors are located along a flexible tube of a device, wherein the sensed values are at least partially due to at least one alternating magnetic field generated by at least one magnetic field generator, the source amplitude and frequency of each generated magnetic field are given to the host server; and calculating by the host server, based on the sensed magnetic field values and the given source amplitude and frequency of each generated magnetic field, a localization of the flexible tube.

43 Claims, 6 Drawing Sheets

(56) References Cited

U.S. PATENT DOCUMENTS

| | | | |
|---|---|---|---|
| 5,646,525 | A | 7/1997 | Gilboa |
| 5,769,843 | A * | 6/1998 | Abela ................... A61B 34/20 606/15 |
| 6,052,610 | A | 4/2000 | Koch |
| 6,073,043 | A | 6/2000 | Schneider |
| 6,833,814 | B2 | 12/2004 | Gilboa et al. |
| 7,536,909 | B2 | 5/2009 | Zhao et al. |
| 8,340,686 | B2 | 12/2012 | Bartlett |
| 8,683,707 | B1 | 4/2014 | Horton, Jr. |
| 8,825,134 | B2 | 9/2014 | Danehorn |
| 9,024,624 | B2 | 5/2015 | Brunner |
| 9,116,198 | B2 | 8/2015 | Cai et al. |
| 9,658,298 | B2 | 5/2017 | Cai et al. |
| 9,763,741 | B2 | 9/2017 | Alvarez et al. |
| 9,839,481 | B2 | 12/2017 | Blumenkranz et al. |
| 10,276,289 | B1 | 4/2019 | Kirby et al. |
| 10,499,993 | B2 | 12/2019 | Chopra et al. |
| 10,524,641 | B2 | 1/2020 | Prisco |
| 10,610,306 | B2 | 4/2020 | Chopra |
| 10,615,500 | B2 | 4/2020 | Morgan et al. |
| 10,704,929 | B1 | 7/2020 | Memarzanjany et al. |
| 2002/0065455 | A1 | 5/2002 | Ben-Haim et al. |
| 2003/0216639 | A1 | 11/2003 | Gilboa et al. |
| 2007/0016007 | A1 | 1/2007 | Govari et al. |
| 2009/0030646 | A1 | 1/2009 | Jones et al. |
| 2010/0082280 | A1 | 4/2010 | Schneider |
| 2011/0085720 | A1 | 4/2011 | Averbuch |
| 2011/0156957 | A1 | 6/2011 | Waite |
| 2011/0275925 | A1 * | 11/2011 | Leichner ................ A61B 5/287 600/407 |
| 2011/0313414 | A1 | 12/2011 | Liu et al. |
| 2016/0015323 | A1 | 1/2016 | Tathireddy et al. |
| 2016/0213430 | A1 | 7/2016 | Mucha |
| 2016/0278746 | A1 * | 9/2016 | Hancu ................. A61B 5/4312 |
| 2017/0090568 | A1 | 3/2017 | Chen |
| 2017/0347915 | A1 | 12/2017 | Weprin et al. |
| 2017/0351094 | A1 | 12/2017 | Poulos et al. |
| 2018/0110562 | A1 | 4/2018 | Govari et al. |
| 2018/0193100 | A1 | 7/2018 | Larkin et al. |
| 2018/0220928 | A1 | 8/2018 | Blood et al. |
| 2018/0221610 | A1 | 8/2018 | Larson et al. |
| 2019/0056243 | A1 | 2/2019 | Foster et al. |
| 2019/0089059 | A1 | 3/2019 | Pelrine et al. |
| 2022/0065661 | A1 | 3/2022 | Barak et al. |

FOREIGN PATENT DOCUMENTS

| | | |
|---|---|---|
| WO | WO 2020/129050 | 6/2020 |
| WO | WO 2021/048837 | 3/2021 |

OTHER PUBLICATIONS

International Search Report and the Written Opinion dated Sep. 9, 2019 From the International Searching Authority Re. Application No. PCT/IL2020/050972. (26 Pages).

International Search Report and the Written Opinion dated Feb. 26, 2020 From the International Searching Authority Re. Application No. PCT/IL2019/051363. (11 Pages).

Rotenberg et al. "Compensation of Magnetic Disturbances Improves Inertial And Magnetic Sensing of Human Body Segment Orientation", IEEE Transactions on Neural Systems and Rehabilitation Engineering, 13(3): 395-405, Sep. 12, 2005.

Strachen et al. "Accurate Indoor Navigation With Spinning Magnets", International Conference on Information Processing in Sensor Networks, IPSN '18, Porto, Portugal, Apr. 11-13, 2018, 2 P., Apr. 11, 2018.

International Preliminary Report on Patentability dated Mar. 17, 2022 From the International Bureau of WIPO Re. Application No. PCT/IL2020/050972. (6 Pages).

Supplementary European Search Report and the European Search Opinion dated Apr. 21, 2022 From the European Patent Office Re. Application No. 19899014.5. (6 Pages).

Supplementary European Search Report and the European Search Opinion dated Sep. 1, 2022 From the European Patent Office Re. Application No. 20862152.4. (7 Pages).

Official Action dated May 24, 2023 From the U.S. Patent and Trademark Office Re. U.S. Appl. No. 17/414,377. (47 Pages).

* cited by examiner

MAGNETIC FLEXIBLE CATHETER TRACKING SYSTEM AND METHOD USING DIGITAL MAGNETOMETERS

BACKGROUND

Known Electromagnetic (EM) localization systems are sometimes used in the Medical field for tracking a small catheter inside the body. The reason EM systems are highly suitable for such applications, is because the body is transparent to EM near-fields. This allows for a catheter or any other tool to be tracked in real-time inside (or outside) the body without the need for a line-of-sight and without the use of any potentially harmful imaging modalities such as X-ray or Computed Tomography (CT).

Some known system may include an EM field sensor/receiver and an EM field generator/transmitter that transmits multiple different alternating ("AC") EM fields, for example sinusoidal EM fields. The receiver usually receives a combination of the multiple EM fields from the transmitter, and differentiates between the different fields, for example by performing a Fast Fourier Transform (FFT) and/or a Discrete Fourier Transform (DFT) or any other suitable method. By analyzing the phases and/or amplitudes, the receiver identifies a unique EM signature associated with a specific position and orientation, e.g. a specific six-degrees-of-freedom (6DOF) state, for example three coordinates of position and three angles of orientation. In other systems the EM signature is used to recover only five-degrees-of-freedom (5DOF). In these systems the roll angle of the sensor is usually absent. In other systems only the position may be solved (3DOF) and the orientation of the sensor remains unknown.

In order to enable decomposition of the received combination of fields and/or distinguishing between the received fields and identification of a unique 6DOF (or 5DOF) state of the monitored object, the transmitter needs to transmit multiple EM sinusoidal field signals in carefully chosen frequencies, for example so that the sinusoidal field signals are orthogonal to each other. Some systems may include N transmitting coils which generate EM fields of different geometry. The number N should be large enough to enable identification of the 6DOF (or 5DOF) state of the monitored object. In other systems, there may be a smaller number of coils that generate orthogonal (at the source) and/or otherwise highly distinctive EM field signals. In order to ease the separation between the fields, and increase the operation rate of the system, the system may usually use high-frequency EM fields, in the kHz scale.

In a traditional EM-tracked catheter setting, a catheter would have one or more micro coils placed at its tip. For example, three micro-sized coils need to be placed at the tip of the catheter, traditionally in an orthogonal manner, and wires need to be pulled outside to an external DSP. In some specialized systems a single coil is used rather than three orthogonal coils, but this requires a specialized EM field generator to generate many different unique fields, and in addition it can only provide localization of up to five degrees-of-freedom (with roll angle missing). In general, one-coil systems are inferior in terms of accuracy and overall stability. The EM field generator would generate a high-frequency (>1 kHz, for example) alternating magnetic field which would induce electromotive force (EMF) on the catheter's coils (by Faraday's law of induction). The coils are connected through wires to an external digital signal processor (DSP) unit which is responsible for amplifying the induced voltage, then sampling it, for example by using an analog-to-digital (AMD) converter. A dedicated processor would then analyze the sensed signal, decompose it using FFT or DFT (or any other suitable method) into separate sine wave amplitudes and pass the DFT results to another processing stage which is responsible for translating the computed field amplitudes into a position and orientation of the sensor in three-dimensional space, relative to the field generator.

The DSP unit should contain high-quality low-noise amplifiers in order to be able to enhance the tiny voltages which are picked up on the micro coils for the A2D converter to be able to sample them with good SNR (Signal-Noise Ratio). Every such coil requires a separate processing channel with a dedicated high-quality amplifier and A2D input. In addition, good signal-noise ratio (SNR) is hard to maintain; the tiniest noise might be amplified and obscure the signal of interest. For example, the wires connecting the coils to the DSP might form a loop through which some magnetic flux flows and which therefore picks up some amount of parasitic, undesired signal from the transmitted fields. This requires the wires to be wound across the catheter in a twisted pair fashion. In addition to the wires, the connector which connects the catheter to the DSP might also form an undesired loop which is able to pick up some amount of parasitic signal. A traditional EM catheter therefore involves a complex design, with a special, complicated and expensive, complementary DSP unit. The complexity of such system grows almost linearly with the number of desired sensors (the number of coils, number of twisted-pair wires, number of DSP input channels which include more expensive amplifiers and A2D). For all these reasons, one should appreciate why constructing a traditional EM catheter with more than just a very few EM sensors is virtually impractical.

Some devices such as mobile phones include an Inertial Measurement Unit (IMU) that provides information of the device's motion and pose. Usually, the IMU includes digital sensors such as a 3-axis accelerometer and a 3-axis gyroscope, and in many cases it also includes a 3-axis magnetometer. The accelerometer senses accelerations in local 3D coordinates. In a normal setting the accelerometer mainly senses the gravity force vector (plus some local, linear acceleration which can be filtered out using various sensor-fusion methods) and therefore may enable detection of partial orientation, for example of the device's screen (landscape/portrait). The gyroscope senses angular velocity of the device. In many applications, the data received from the accelerometer and the gyroscope are combined to provide robust orientation tracking of the device. Since these two sensors have no reference except for the gravity force (which points to the sky), the orientation computed from the accelerometer and the gyroscope usually drifts slowly around the gravity vector. In this sense, orientation tracking based on accelerometer and gyroscope alone is considered "drifting", since it has no stable reference. The magnetometer may be used to sense the DC Earth's magnetic field, for example using Hall effect sensors, magneto-resistive sensors, magneto-inductive sensors, and/or by any other suitable sensor type. The sensed DC Earth's magnetic field may be used to correct drifting of the accelerometer and gyroscope orientation detection in Earth coordinates. However, the magnetometer readings are often distorted by various elements in its environment, such as nearby metals (soft-iron, hard-iron distortion). In addition, low-cost magnetometer sensors are prone to bias calibration problems, where the internal bias of the sensor drifts over time. Therefore, in many applications the magnetometer data is ignored and orientation is detected by the accelerometer and gyroscope only, although the identified orientation usually drifts over time with respect to Earth's North, since the magnetometer data is dismissed and no other sensor is used as an additional reference for orientation. While the IMU is mostly used for orientation detection, it may also be used for relative positioning. Using sensor fusion methods, the local acceleration may be extracted from the accelerometer readings (subtracting the gravity force). It can be then integrated over short time periods to compute the velocity of the device. Double integration gives relative position of the device. These methods, however, are highly sensitive to bias noise and are therefore usually only used with high-end highly accurate IMU sensors or over very short time periods (for example, for motion gesture detection). While the IMU can be used in a normal setting for computing absolute orientation of a device relative to Earth's coordinates (by using data from all 3 sensors: accelerometer, gyroscope and magnetometer), none of the IMU readings provide any information of device's position relative to any absolute reference. In order to use the IMU for accurate absolute positioning, some external reference must be added.

SUMMARY

An aspect of some embodiments of the present invention provides a method for magnetic tracking of a flexible catheter device or another flexible elongated device, the method comprising: receiving by a host server a plurality of sensed values of a local magnetic field, sensed by a respective plurality of sensors, wherein the host server is optionally included in a controller of the sensors, the sensors are located along a flexible tube of a device, wherein the sensed values are at least partially due to at least one alternating magnetic field generated by at least one magnetic field generator, the source amplitude and frequency of each generated magnetic field are given to the host server; and calculating by the host server, based on the sensed magnetic field values and the given source amplitude and frequency of each generated magnetic field, a localization of the flexible tube.

Optionally, the method includes receiving by a host server, from at least one generator of an alternating magnetic field, a momentary phase value of the generated magnetic field; associating by the host server between the momentary phase value and at least some of the sensed magnetic field values received from the sensors; and calculating by the host server, based on the magnetic field values and the associated phase value, a localization of the flexible tube.

Optionally, the associating is based on a corresponding clock reading shared or synchronized among the magnetic field generator, the controller of the sensors and the host server.

Optionally, the phase data is received from the at least one generator in full rate of a magnetometer located at the at least one generator.

Optionally, the clock reading is shared by the magnetic field generator or by a clock source shared among the field generator, a controller of the sensors and the host server.

Optionally, the method includes receiving from the at least one generator an amplitude value of the generated magnetic field at the source.

Optionally, the calculating includes calculation of position and orientation of each of the plurality of sensors.

Optionally, the calculating includes using an Extended Kalman filter for fusing sensor data and imposing a motion model or shape constraints on the calculations.

Optionally, wherein at least one of the sensors is a sensor bundle, and the calculation incorporates accelerometer or gyroscope readings of corresponding sensors included in the sensor bundle.

Optionally, the calculation incorporates known structural relationships between the sensors to calculate an estimation of the position, orientation or curve of the tube as a whole.

Optionally, the sensed values are at least partially due to at least two generated magnetic fields generated by at least two corresponding generators.

Optionally, the at least two generated magnetic fields operate at different frequencies.

Optionally, the at least two generators share the same clock or have synchronized clocks or share a clock source.

Another aspect of some embodiments of the present invention provides a system for magnetic tracking of a flexible catheter device or another flexible elongated device, the system comprising: at least one generator, each configured to generate an alternating magnetic field wherein each generated magnetic field has a determined source amplitude and frequency; a device comprising: a flexible tube; a plurality of sensors, the sensors are located along the flexible tube, each configured to communicate sensed values of a local magnetic field, wherein the sensed values are at least partially due to the generated magnetic field; and a host server configured to: receive the sensed local magnetic field values from the corresponding sensors; and calculate, based on the magnetic field values and the determined source amplitude and frequency, a localization of the flexible tube, wherein the host server is optionally included in a controller of the sensors.

Optionally, the host server is configured to receive, from at least one generator of an alternating magnetic field, a momentary phase value of the generated magnetic field; associate by the host server between the momentary phase value and at least some of the sensed magnetic field values received from the sensors; and calculate by the host server, based on the magnetic field values and the associated phase value, a localization of the flexible tube.

Optionally, the associating is based on a corresponding clock source reading shared among the magnetic field generator, a controller of the sensors and the host server.

Optionally, the device further comprises a flexible PCB along the tube, wherein the sensors are located along the flexible PCB.

Optionally, the flexible PCB is wrapped in a helix manner on a wall of the tube.

Optionally, the device further comprises a communication bus configured to carry the sensed values data digitally from the plurality of sensors towards the server.

Optionally, the communication bus includes up to four wire lines that may carry the sensed values digital data from and provide power to the plurality of sensors.

Optionally, the at least one generator comprises an internal clock and is configured to share its clock readings with the sensors and with the host server.

Optionally, the at least one generator comprises a magnetometer configured to detect the phase data.

Optionally, at least one of the sensors is a sensor bundle comprising accelerometer or gyroscope sensors.

Optionally, the system includes at least two generators that generate at least two respective magnetic fields that operate at different frequencies.

Optionally, the at least two generators share the same clock or have synchronized clocks or share a clock source.

Optionally, the at least one generator comprises at least one permanent magnet and a motor device that rotates the magnet in a determined frequency.

Optionally, the at least one generator comprises an electromagnetic coil that generates a sinusoidal electromagnetic field at a specific known frequency.

Optionally, the device includes a plurality of dipole magnets positioned between the sensors.

Optionally, the dipole magnets are positioned in equal distances and oriented so that two magnets located at two sides of a sensor have opposite dipole directions, when the tube is in a straight state.

BRIEF DESCRIPTION OF THE DRAWINGS

Some non-limiting exemplary embodiments or features of the disclosed subject matter are illustrated in the following drawings.

In the drawings.

Figure 1:
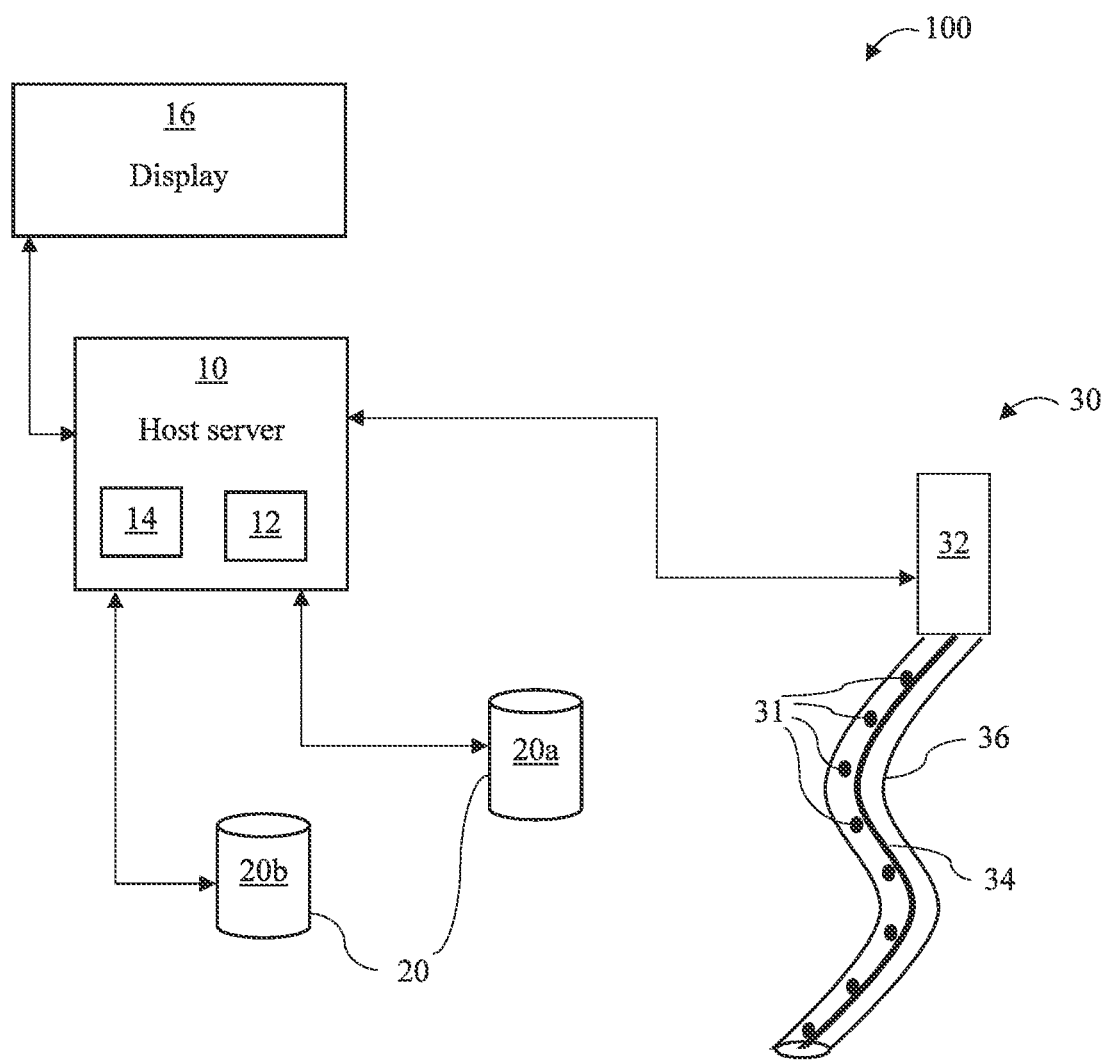
FIG. 1 is a schematic illustration of a catheter tracking system for tracking by digital magnetometers, according to some embodiments of the present disclosure.

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

Some embodiments of the present disclosure provide a magnetic full-curve catheter tracking system. A magnetic field generator/transmitter according to some embodiments of the present disclosure may induce electromagnetic field on a plurality of magnetometers placed along a flexible catheter tube. In some embodiments, the provided system may include at least one special magnetic field generator and/or use a special magnetic field generation and/or transmission method. A magnetic field generator/transmitter provided according to some embodiments of the present invention may consist of low-cost components.

The provided system may receive sensor readings of local electromagnetic field values from the plurality of magnetometers, and based on the received readings calculate a full-curve localization of the catheter tube along its length. This is in contrast to traditional EM catheter tracking systems in which, usually, only the catheter tip is tracked. In some embodiments, the provided system may calculate and/or identify 6DOF localization, e.g. three-dimensional position and orientation, of each magnetometer based on its magnetic sensor reading, relative to the magnetic field generator(s). In some embodiments, the sensing radius of the magnetometers is up to about 50 centimeters. Accordingly, in some embodiments, the distance of the at least one magnetic field generator from the plurality of magnetometers is up to 50 centimeters.

According to some embodiments, the provided system includes a plurality of digital magnetometers, for example off-the-shelf magnetic sensors, for example similar to or the same magnetometers included in IMUs. In some embodiments, full IMU sensor bundles are used. The digital magnetometers may have a small footprint and/or size, suitable for catheters for insertion into various body cavities. For example, the magnetometers are insertable to a catheter tube and/or to a body cavity and/or on the catheter tube wall. For example, the plurality of magnetometers may be placed, for example in an integrated circuit and/or silicon die, on a flexible printed circuit board (PCB) along the catheter tube. The plurality of magnetometers may be packaged, for example in an Ultra-Small Wafer Level BGA (Ball grid array) package. This may allow for placing them on a very thin flexible PCB.

A magnetometer, as referred to throughout the present description, usually operates at a sampling rate of an order of magnitude of hundreds of Hz, for example of about 100 Hz and/or up to 500 Hz-1000 Hz. In order to use a direct-current (DC) magnetometer (one that measures DC magnetic fields) as an alternate-current (AC) magnetic sensor (one that is intended for use with AC magnetic fields), the sensed AC magnetic field may be of a frequency significantly smaller than the magnetometer's sampling rate, e.g. an order of magnitude smaller. The sensed magnetic fields should be in a range detectable by the DC magnetometer. For example, the sensed magnetic field should be about ten times the magnetometer's sensitivity when generated, and take into account also the noise level, in order to be detected by the magnetometer. For example, a DC magnetometer can detect magnetic fields of between a few $\mu T$ to a few thousands of $\mu T$ (For example, between 1 to 4000 $\mu T$) with sensitivity, e.g. resolution, of about 0.1 $\mu T$. Since a magnetic field's strength is inversely proportional to the cube of the distance between the dipole source and the receiver, the sensing range should have a factor −10 between the minimal to the maximal distances, for example 10 cm to 1 m or 1 m to 10 m, etc.

According to some embodiments, the plurality of magnetometers are placed along and transmit the sensed values by a same data bus, requiring, for example, as few as four or less electrical wires pulled along the catheter tube, no matter how many magnetometers are placed along and/or transmitting the data by the data bus. This is in contrast to traditional analog catheter tracking systems, that may require a number of wires that grows linearly with the number of magnetic sensors.

Some embodiments of the present disclosure provide a method for localization calculation that may calculate the full-curve localization of the catheter curve in a rate greater than 30 Hz. This rate is suitable for most real-time medical applications. Therefore, some embodiments of the present invention provide a solution to the problem of acquiring real-time full-curve localization of a small-diameter catheter, without the high costs of traditional EM sensors and DSPs. Additionally, in some embodiments the provided system has low power consumption, for example both on the receiving and the transmitting end, which may allow for a wireless and/or battery operated full-curve catheter localization system of a significantly small footprint.

The ability to construct a full curve tracked catheter at low costs and uncomplicated configuration, as provided by some embodiments of the present disclosure, is important for many potential medical applications.

Reference is now made to FIG. 1, which is a schematic illustration of a catheter tracking system 100 for tracking by digital magnetometers, according to some embodiments of the present disclosure. According to some embodiments of the present disclosure, system 100 provide a solution for full-curve catheter localization. System 100 may include a catheter 30, a hardware host server 10 and at least one magnetic field generator/transmitter 20, for example, magnetic field generators/transmitters 20a and 20b. As described herein, system 100 may provide a full curve localization of catheter 30 to its length. In some embodiments of the present disclosure host server 10 is included in a controller in catheter 30, e.g. all the functionalities of host server 10 described herein are performed by a controller in catheter 30. The terms controller and microcontroller are sometimes used interchangeably throughout the present disclosure and may also mean or include a microprocessor.

Transmitter 20 may generate a magnetic field. For example, transmitter 20 is an electromagnetic generator of magnetic fields, for example including at least one electromagnetic coil. Each generator 20 may generate an alternating magnetic field. Each generated magnetic field has a determined source amplitude and frequency. In some embodiments, transmitter 20 may include a sensor that senses a momentary phase of the generated EM field or computes the momentary phase of the generated EM field by using a synchronized EM field generator driver and communicates to host server 10, for example, periodically, the momentary phase value along with a timestamp.

Figure 2:
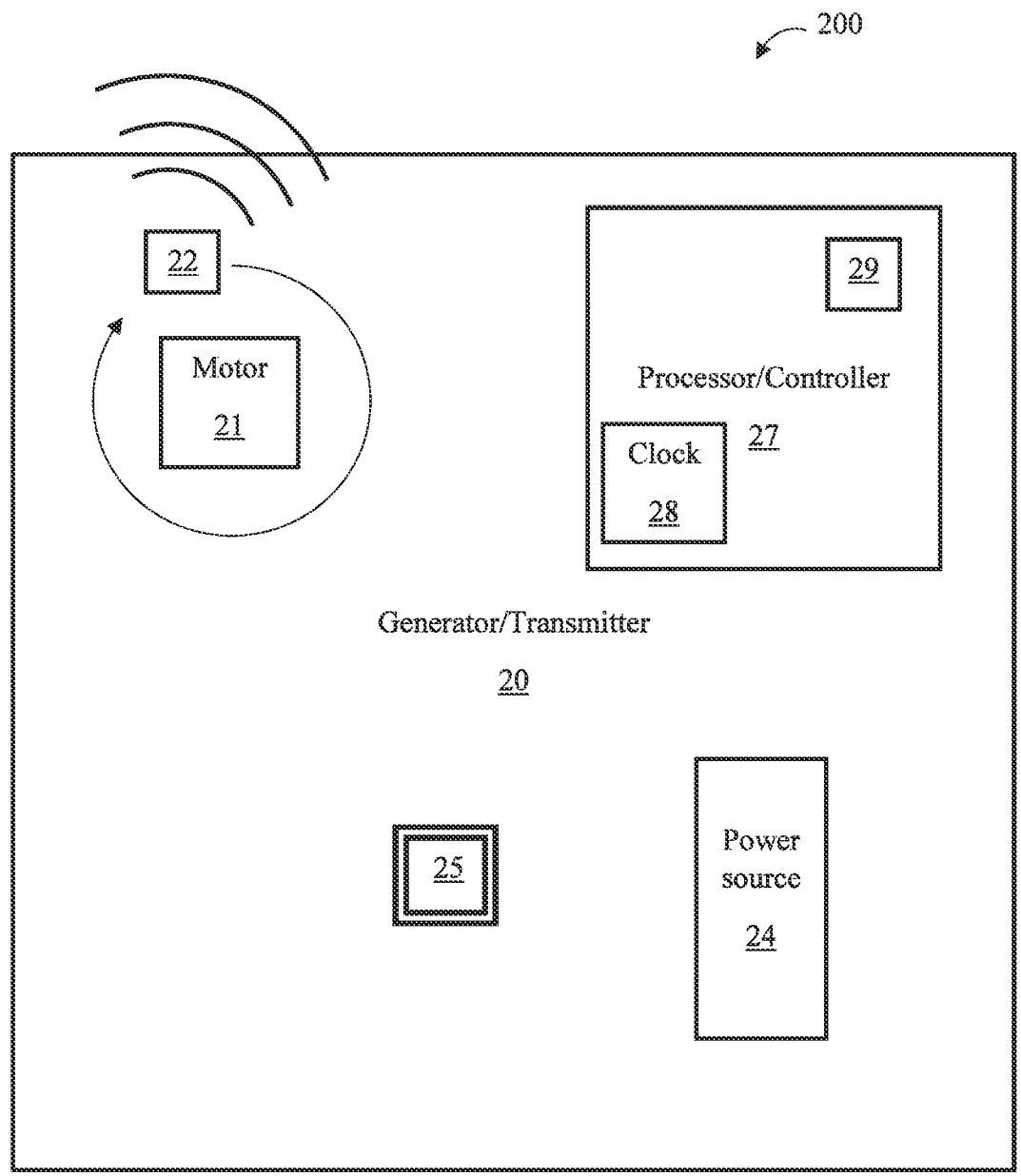
FIG. 2 is a schematic illustration of an exemplary magnetic field generator/transmitter for tracking by digital magnetometers, according to some exemplary embodiments of the present disclosure.

In some embodiments of the present disclosure, transmitter 20 may include at least one rotating magnet, as shown in more detail in FIG. 2. As described in more detail herein, in some embodiments, transmitter 20 may include a sensor that senses a momentary phase of the rotating magnet or computes the momentary phase of the rotating magnet by using a synchronized motor driver and communicates to host server 10, for example, periodically, the momentary phase value along with a timestamp.

Catheter 30 may include a microcontroller 32, a flexible tube 36 and a plurality of magnetometer sensors 31, for example implemented upon a flexible PCB (shown in more detail in FIG. 4) along tube 36. Magnetometer sensors 31 may be placed in predefined locations along tube 36 and/or in predefined distances between them. According to some embodiments, magnetometer sensors 31 may be or include off-the-shelf magnetic sensors, for example similar to or the same magnetometers included in IMUs or standalone off-the-shelf magnetic sensors. In some embodiments, each of magnetometer sensors 31 may be or include a full IMU sensor bundle.

Each of magnetometer sensors 31 may sense a corresponding local magnetic field value resulting from the magnetic field generated by transmitter 20. Host server 10/microcontroller 32 may receive the magnetic field value from sensors 31 and/or microcontroller 32 may communicate to host server 10/microcontroller 32 the sensed value along with a timestamp. Microcontroller 32 may be located at a proximal end of catheter 30, e.g. in a communication path between sensors 31 and host server 10. For example, microcontroller 32 may receive and/or gather at least one local and momentary magnetic field values from respective at least one sensor 31, for example values sensed in a certain moment, and transmit the gathered values along with a corresponding timestamp, for example, over USB, wireless communication, etc. For example, microcontroller 32 may communicate the gathered sensed values along with identification of the respective sensing sensors 31, for example for each sensed value. As described in more detail herein, sensors 31 may be communicationally connected by a same data bus 34 placed along tube 36, to microcontroller 32 and/or to host server 10. In some embodiments of the present disclosure, at least some of the functionalities of host server 10 described throughout the present description are performed by microcontroller 32. In some embodiments, all functionalities of host server 10 are performed by microcontroller 32 and/or processor/controller 27 described with reference to FIG. 2.

Flexible tube 36 may be positioned in various positions and may have various momentary curve shapes, for example according to a shape of a body organ it is inserted into and/or according to obstacles the catheter tube encounters.

Host server 10/microprocessor 32 may include at least one hardware processor 12 and/or at least one hardware memory 14. Memory 14 may include a tangible non-transitory processor readable storage medium, storing processor readable program instructions thereon, for causing processor 12 to carry out aspects of the present disclosure. System 100 may include a display device 16, configured to receive data and/or instructions from host server 10 and display information according to the received data and/or instructions. Display device 16 may show, for example, navigational instructions for instructing the physician to reach a certain point of interest inside the body.

Magnetometer sensors 31 may be and/or include digital magnetometers configured to provide sensor digital output, may be low-cost and/or may have a small footprint. In some embodiments, each of sensors 31 may be or include a standard IMU, which may include a magnetometer, an accelerometer and/or a gyroscope. The plurality of sensors 31 may be placed along a same digital communication bus 34 and/or communicate the sensor digital output by same digital communication bus 34 to microcontroller 32 and/or to server 10. For example, sensors 31 may sense along the curve of tube 36 local electromagnetic field values simultaneously or within a very short period of milliseconds, and/or may transmit these values by the same bus 34 to microcontroller 32 and/or to server 10, for example simultaneously or within a very short period of up to a few milliseconds or a few tens of milliseconds. Host server 10/microprocessor 32 may receive the sensed local magnetic field values from the corresponding sensors 31, and/or may calculate a localization of flexible tube 36, for example based on the sensed magnetic field values and the determined source amplitude and frequency of the magnetic field generated by transmitter 20

Each sensor 31 may be identified separately by microcontroller 32 and/or server 10. For example, microcontroller 32 and/or server 10 may relate each received electromagnetic field value to the respective sensor 31 that sensed this value. For example, microcontroller 32 may transmit the sensed value to server 10 along with an identifier code that identifies the sensor that sensed this value. In some embodiments, the sensed value and/or identifier code is sent along with a timestamp which, for example, attests to the reading time of the sample. As described in more detail herein, host server 10/microprocessor 32 may calculate 6DOF localization of the respective sensor based on the received sensed value and/or timestamp and/or the phase data received from at least one generator 20, and/or calculate a full-curve position of catheter tube 36 based on the plurality of sensed values received from the plurality of sensors 31. For example, the calculation is made by imposing some shape and/or curvature constraints. In some embodiments of the present invention, system 100 may include any suitable number of sensors 31 along tube 36, for example with no substantial increase to the complexity of the system, for example since sensors 31 transmit the sensed values by the same data bus 34. For example, in some embodiments, no DSP input channels are required in order to amplify, sample and transmit the magnetic values from sensors 31 to microcontroller 32 and/or server 10.

In some embodiments, system 100 is synchronous, e.g. shares a single clock between its components. For example, generator/transmitter 20 may include an inner clock, and/or may share its clock readings with sensors 31, microcontroller 32 and/or with server 10 and/or with other generator/transmitters, as described in more detail herein. In some embodiments of the present disclosure, at least some of the components of system 100 synchronize their respective clocks with an external clock. Microcontroller 32 may receive from sensors 31 their respective sensed values. For example, microcontroller 32 may receive via data bus 34 the sense data sampled by sensors 31 and written on data bus 34. In some embodiments, microcontroller 32 transmits the data to host 10, for example along with a corresponding timestamp. For example, the timestamp corresponds to respective clock readings received from transmitter 20, or is based on another shared clock. Server 10 may receive the data from transmitter 20 and sensors 31 and/or synchronize the data according to the timestamps. For example, the shared or external clock may include a dedicated crystal oscillator physically connected to all devices, a USB hub clock shared among all devices connected to the USB hub, a clock generated by an RF (radio-frequency) main source and shared wirelessly among RF devices, or a GPS clock, sensed by at least some devices in system 100.

In some exemplary embodiments, transmitter 20 may use electromagnetic coils to generate low-frequency magnetic fields. The frequency may be low enough (for example, lower than 500 Hz) to be fully matched by the sampling rate of sensors 31, e.g. sensors 31 may sample the magnetic fields in at least a minimum rate required for retaining all the required information, for example amplitude, frequency and/or phase, about the sensed magnetic field. The generated magnetic fields may be strong enough within the sensing radius (for example, stronger than 1 uT) to get quality samples, in magnetometer's sensitivity and/or signal-to-ratio ("SNR") sense. Sensor 31 may collect enough samples to perform discrete Fourier transform ("DFT") or similar algorithms to separate between the generated magnetic fields and solve for 6DOF localization of sensors 31 and/or tube 36. In some cases, in order to provide low-latency, high-rate 6DOF solutions, phase information may be provided by transmitter 20 and synced between transmitter 20 and sensor 31 and/or microcontroller 32. This way, microcontroller 32 and/or host server 10 may be aware of a momentary phase of the generated magnetic field, and may be able to produce rapid 6DOF solutions by using the synchronized phase information and timestamps in an extended Kalman filter setting (as explained herein).

As described in more detail herein, for example with reference to FIG. 2, according to some embodiments of the present invention, magnetic field generator/transmitter 20 includes a rotating magnet and a rotary sensor, e.g. a magnetometer, that senses the momentary phase of the magnet rotation, e.g. where the magnet is located in its rotational orbit in a given moment. For example, the rotary sensor is configured to communicate to server 10 the momentary phase information, for example along with respective timestamps of the clock readings, for example in full rate.

For example, according to their matching timestamps, server 10 may relate a certain phase state of the generated magnetic field(s) to corresponding local magnetic field readings received from sensors 31, which were sensed and/or transmitted at the same time as the phase reading. Based on the magnetic field readings and the related momentary phase reading(s), server 10/microprocessor 32 may calculate the full-curve catheter localization, for example in real time. For example, host server 10/microprocessor 32 may receive from at least one generator 20 of an alternating magnetic field, a momentary phase value of the generated magnetic field, may associate between the momentary phase value and at least some of the sensed magnetic field values received from sensors 31, and/or may calculate, based on the magnetic field values and the associated phase value, a localization of flexible tube 36.

It will be appreciated that system 100 may include a plurality of catheters 30, and that server 10 may calculate the full-curve catheter localizations for a plurality of catheters 30, for example concurrently.

Reference is now made to FIG. 2, which is a schematic illustration of an exemplary magnetic field generator/transmitter 20 for tracking by digital magnetometers, according to some exemplary embodiments of the present disclosure. Generator/transmitter 20 may include at least one permanent magnet 22, a processor/controller 27 having an inner clock 28 and a communication interface 29, a motor device 21, a magnetometer 25, and a power source 24.

The configuration of generator/transmitter 20 as shown in FIG. 2 and described herein is not required by some embodiments of the present invention, and other suitable configurations, components and/or structures of generator/transmitter 20 are possible, according to some embodiments of the present invention.

In some embodiments, generator/transmitter 20 generates a low-frequency electromagnetic field of, for example, less than 60 Hz, having strength of, for example, about 1 uT or stronger at, for example, about 1 meter from the transmitter.

Usually, in order to produce such a strong field by an AC current according to Ampere's law, a very large transmitter with very high-power consumption is required. However, according to some embodiments of the present invention, generator/transmitter 20 includes at least one permanent magnet 22 that generates the magnetic field. By producing the magnetic field by at least one permanent magnet, the magnetic field produced by generator/transmitter 20 may be about a hundred times stronger than a magnetic field produced by AC electric current, by a transmitter of similar dimensions, and results in an extremely low-power transmitter. The material of the magnet is chosen to maximize the generated magnetic field strength compared to the size of generator/transmitter 20. For example, generator/transmitter 20 may include a rare-Earth magnet, for example a Neodymium magnet or magnet of another suitable material.

In order to produce an AC magnetic field, in some embodiments of the present invention, magnet 22 is mounted on an axis rotated, for example, by a motor device 21, for example a direct-current (DC) motor, or by electromagnetic coils wound around magnet 22 which produce a weak AC field, strong enough to rotate the magnet at their center with their applied torque, or by off-the-shelf electromagnetic single-axis coils placed near magnet 22 which produce a weak AC field, strong enough to rotate the magnet with their applied torque, or any other suitable device, at a desired operating frequency f. Thus, for example, rotating magnet 22 results in an AC magnetic field in the surrounding space. The magnetic field generated by the rotating magnet 22 may be expressed as the superposition of two AC magnetic fields of frequency f and orthogonal phases and generated by two separate virtual coils x and y:

$$B(\vec{r},t)=B_x(\vec{r})\cos(\phi(t))+B_y(\vec{r})\sin(\phi(t))$$

where $\phi(t)$ is the phase within the rotation of the magnet 22. In a perfect setting $\phi(t)=\omega t$, that is, the transmitter produces perfectly fixed frequency $\omega=2\pi f$, but in more practical scenarios this is just an approximation which can be expressed as: $\phi(t)\approx\omega$. $B_x$ is the magnetic dipole field due to the 'x' virtual coil and $B_y$ is the magnetic dipole field due to the 'y' virtual coil. In other words, $B_x$, $B_y$ are two magnetic fields corresponding to virtual 'x' and 'y' axes of the rotating magnet 22, respectively. It will be appreciated that according to some embodiments of the present invention, magnet 22 may be controlled to move according to other, for example more complicated, motion models. For example, magnet 22 may be rotated about a time-varying axis direction. For example, the movement of magnet 22 may include a combination of rotational motion about a fixed axis and a periodic linear motion parallel to the fixed axis. Other motion models are also in the scope of the present invention. In some embodiments, the more complicated motion models may add an additional orthogonal virtual coil 'z' whose dipole field is denoted $B_z(\vec{r})$ and that may enhance the position and orientation calculations. This is while keeping the ability of magnetometer 25 to detect the momentary position, e.g. phases, of magnet 22.

In some embodiments, magnet 22 may be controlled by generator 20 to rotate about an additional, secondary, axis, to obtain a more complex magnetic field sensed by receiver 20 and thus, for example, provide more information for the position and orientation calculation. Magnetometer 25 may sense the corresponding generated magnetic fields and accordingly calculate momentary phases of magnet 22, in the rotational motions about the first axis and the secondary axis, and transmit the calculated momentary phases to receiver 20. For example, the cyclic motion of magnet 22 is produced by mounting magnet 22 and/or a first motor on a camshaft of a second motor. For example, the cyclic motion about the first and second axes is applied to magnet 22 by mounting magnet 22 on a shaft, the shaft is free to rotate and move axially and includes a radial pin engaged in a groove in a surrounding sleeve. Optionally, the groove is in the shaft and the pin extends from the sleeve radially into the groove.

Processor/controller 27, for example a microcontroller/controller, may maintain a permanent desired frequency f, in which motor 21 operates and/or magnet 22 rotates. For example, a desired frequency f is inherent to and/or embedded in the hardware of controller 27 and/or transmitter 20. For example, motor device 21 may be a highly stable motor and/or or a specially designed motor, for example, operating according to a clock 28 of controller 27, or otherwise maintaining a substantially constant frequency. In some embodiments, controller 27 may switch between various possible frequencies to maintain, for example by maintaining corresponding voltage levels provided to motor 21, in a closed feedback loop with the transmitter's magnetometer 25 (rotary sensor), causing transmitter 20 to generate AC field in a desired maintained frequency f. In some embodiments, controller 27 may include hardware and/or software components to change the frequency f. The maintained frequency f may be communicated to receiver/sensor 20, for example by controller 27, for example by communication interface 29. Communication interface 29 may include a low-power radio transmitter/receiver, for example a 2.4 GHz transmitter/receiver, and/or a Low-Energy Bluetooth device, a WiFi communication device, a USB cable, or any other suitable communication device.

According to some embodiments of the present invention, magnetometer 25 may be located at a fixed location relative to rotating magnet 22. Magnetometer 25 may sense the rotation periods of magnet 22 and where in the period magnet 22 is located, e.g. the momentary rotational phase $\phi(t)$ of magnet 22. As indicated in more detail herein, the rotational phase of magnet 22 may include one or two rotation phases about corresponding one or two axes. For example, magnetometer 25 may provide an estimation of the phase of magnet 22, for example by principle component analysis (PCA) of magnetic samples collected over many rotation periods, for example to extract the axes of an ellipse drawn in a local coordinate system centered at transmitter 20 by rotating magnet 22, or any other suitable method for detecting the phase of magnet 22, for example, by fitting an ellipse to samples collected over many periods of the rotating magnet by means of optimization. According to some embodiments of the present invention, magnetometer 25 is placed at and/or on the rotation axis of the rotating magnet. Due to symmetry, the sensed magnetic field forms an approximate circle or ellipse at the location of magnetometer 25 while the magnet is rotating. The formed ellipse/circle may be identified, for example by server 10/microcontroller 32. For example, an ellipse/circle may be fitted to the periodic curve shape of the sensed magnetic field, for example by host server 10/microprocessor 32. For example, server 10/microprocessor 32 may approximate the periodic curve shape of the sensed magnetic field to a circle and/or compute the momentary phase state of the generated magnetic field within this circle.

The rotation frequency of the magnet 22 may be significantly lower relative to the sampling rate of magnetometer 25, e.g. a sampling rate in the range of about 100 Hz-1000 Hz, for example so that the rotation phase of magnet 22 can be estimated more accurately. Therefore, in some embodiments of the present invention, the rotation frequency of magnet 22 is much lower than the sampling rate of magnetometer 25, for example an order of magnitude lower, for example up to about 10 Hz-100 Hz, according to the sampling rate of magnetometer 25. Accordingly, processor/controller 27 may calculate the rotation phase of magnet 22 and/or communicate the calculated phase to receiver server 10, for example by interface 29. Magnetometer 25 may, in some embodiments, be included in a sensor bundle, for example an IMU chip.

According to some embodiments of the present disclosure, unlike traditional magnetic/electromagnetic field transmitter units, transmitter 20 may generate the magnetic field without using electric current to induce magnetic field. Transmitter 20 utilizes the already existing field generated by permanent magnet 22. Therefore, the power consumption of transmitter 20 is much lower compared to traditional transmitter units, the lower consumption allows it to operate, for example, tens of hours on a few standard batteries. Thus, for example, power source 24 that may provide power to transmitter 10 may be a low-power source such as disposable and/or rechargeable batteries and/or any other suitable low-power source. Rotating the magnet either using a standard DC motor or by weak AC fields produced by coils at the proximity of the magnet, which apply torque on the magnet and cause it to rotate, consumes much less power than generating the same AC field using a standard EM transmitter.

Figure 3:
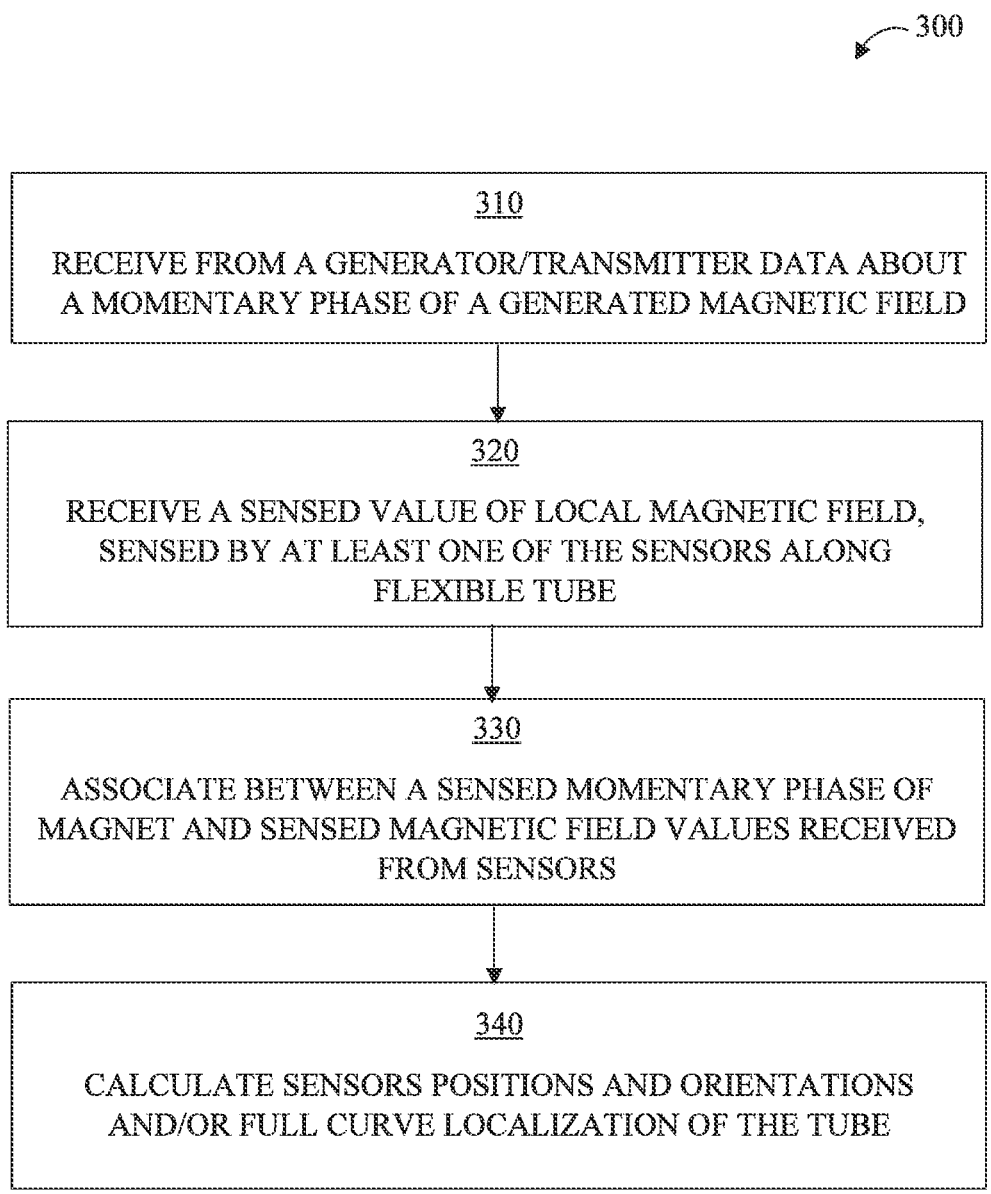
FIG. 3 is a schematic flowchart illustrating a method for tracking by digital magnetometers according to some embodiments of the present disclosure.

Reference is now made to FIG. 3, which is a schematic flowchart illustrating a method 300 for tracking by digital magnetometers according to some embodiments of the present disclosure. As indicated in block 310, server 10 may receive from generator/transmitter 20 data about a momentary phase of a generated alternating magnetic field, for example a momentary rotation phase of permanent magnet 22, for example along with a corresponding clock reading of clock 28. For example, server 10 may receive the phase data from generator/transmitter 20 in predetermined periods and/or each time magnetometer 25 detects a phase of the generated alternating magnetic field. Additionally, server 10 may receive and/or extract the amplitude and/or of the generated magnetic field at the source, i.e. at transmitter 20, for example from magnetometer 25 and/or by pre-defined calibration data stored in server 10.

As indicated in block 320, server 10 may receive a sensed value of local magnetic field, sensed by at least one of sensors 31 along flexible tube 36 that senses the magnetic field generated by generator/transmitter 20. Since sensor 31 senses the generated magnetic field in its local coordinate system, the magnetic field reading is rotated according to its orientation with respect to generator/transmitter 20, yielding, for example, the following magnetic field measurement by sensor 31:

$M_{RX}(t)=R^t(t)M(t)+M_0$

Where R is a 3×3 matrix, representing the orientation of sensor 31 in coordinates of generator/transmitter 20, $M_0$ is a sensor bias of sensor 31, and M(t) is the generated magnetic field, for example plus environmental magnetic field at the location of sensor 31, in coordinates of the generator/transmitter 20.

In case of a single generator/transmitter 20 included in system 100, in some embodiments of the present invention, the local magnetic field at the location of one of sensors 31 can be expressed as the superposition of two AC magnetic fields of frequency f and orthogonal phases and generated by two separate virtual coils x and y of transmitter 20:

$M(t)=B_0+B_x(\vec{r}(t))\cos(\phi(t))+B_y(\vec{r}(t))\sin(\phi(t))$

Where $B_0$ is environmental magnetic field (e.g. Earth's magnetic field), $B_x$, $B_y$ are the magnetic fields due to the virtual coils of generator/transmitter 20, $\vec{r}(t)$ is the position at time t of sensor 31 and $\phi(t)$ is the sensed phase of generator/transmitter 20 at time t (sensed, for example by magnetometer 25). Accordingly, the sensed magnetic field $M_{RX}(t)$ conveys and/or enables extraction, for example by server 10, of the position and orientation of sensor 31, wherein the phase $\phi(t)$ is received from generator/transmitter 20, and wherein time t is the shared reading of clock 28 or of an external clock source shared among at least some of the components of system 100.

As indicated in block 330, server 10 may associate between a sensed momentary phase of magnet 22, sensed and/or communicated by magnetometer 25 and/or generator/transmitter 20, and sensed magnetic field values received from sensors 31, based on the corresponding shared clock reading of clock 28 or of an external clock source shared between components of system 100, such as server 10 and sensors 31 and/or microcontroller 32.

As indicated in block 340, server 10 may calculate, based on the received sensed magnetic field values and the associated phase of magnet 22, position and orientation of sensors 31 that provided a sensed magnetic field value, for example the 6DOF or 5DOF localization of each of sensors 31 and/or an overall position, orientation and/or curve of tube 36. According to some embodiments, server 10 may use for the localization calculations accelerometer and/or gyroscope readings of corresponding sensors included in sensors 31, in some embodiments of the present disclosure.

According to some embodiments of the present disclosure, sensors 31 are required to have minimal size and thus, for example, may not include gyroscope and/or accelerometer and/or other additional sensors. In such cases, system 100 may include more than one generators/transmitters 20, for example generators/transmitters 20a and 20b, for example in order to enable a more accurate calculation of 6DOF or 5DOF localizations.

Generators/transmitters 20a and 20b may both generate alternating magnetic fields, for example in different frequencies (which are not necessarily orthogonal). Generators/transmitters 20a and 20b may be located in a fixed position and orientation relative to each other, and/or the relative position and/or orientation of generators/transmitters 20a and 20b may be computed and/or adjusted, for example by manual and/or computerized calibration.

Similarly to a single generator/transmitter 20, generators/transmitters 20a and 20b may generate magnetic fields $M_1(t)$ and $M_2(t)$, respectively, that may be expressed by:

$M_1(t)=B_{x1}(\vec{r}_1(t))\cos(\phi_1(t))+B_{y1}(\vec{r}_1(t))\sin(\phi_1(t))$ $M_2(t)=B_{x2}(\vec{r}_2(t))\cos(\phi_2(t))+B_{y2}(\vec{r}_2(t))\sin(\phi_2(t))$ Wherein $\vec{r}_1(t)$, $\vec{r}_2(t)$ are the position of sensor 31 in coordinates of transmitter 20a and 20b, respectively, $\phi_1(t)$, $\phi_2(t)$ are the phases tracked by magnetometers 25 of transmitter 20a and 20b, respectively, $B_{x1}$, $B_{y1}$ are magnetic fields due to virtual coils of transmitter 20a and $B_{x2}$, $B_{y2}$ are magnetic fields due to virtual coils of transmitter 20b. Generators/transmitters 20a and 20b may share the same clock and/or have synchronized clocks.

The magnetic field sensed by sensor 31 may be expressed by:

$$M_{RX}^{(DUAL)}(t)=M_0+R_1^t(t)B_0+R_1^t(t)M_1(t)+R_2^t(t)M_2(t)$$

Where $R_1$ and $R_2$ are 3×3 matrices, representing the orientation of sensor 31 in coordinates of generator/transmitter 20a and 20b, respectively, $B_0$ is the environmental magnetic field (e.g. Earth's magnetic field) and $M_0$ is a sensor bias of sensor 31. Since the positions of generators/transmitters 20a and 20b are fixed with respect to each other, $R_2$ and/or $\vec{r}_2$ can be easily derived from $R_1$ and/or $\vec{r}_1$, or vice versa, for example, by the simple relation:

$$T_{12} \cdot [R_1; r_1] = [R_2; r_2]$$

where $T_{12}$ is a known rigid transform which converts the coordinates of transmitter 20a to the coordinates of transmitter 20b, or vice versa. Therefore, when system 100 includes two generators/transmitters 20a and 20b, there may be no need for solving corresponding two relative positions and two relative orientations for each sensor 31. It may suffice to solve position and orientation relative to a first transmitter, which may be converted to the second transmitter's coordinate system. Hence, server 10 may calculate the 6DOF position and orientation of sensor 31 based on the received sensed magnetic field $M_{RX}^{(DUAL)}$ and the sensed magnetic field phases and clock readings received from generators/transmitters 20a and 20b, for example be a catheter localization algorithm implemented in server 10/microcontroller 32.

It will be appreciated that the solution for the 6DOF localization of sensors 31 and/or tube 36 is flexible enough and does not rely on any specific implementation, structure and/or configuration of transmitters 20, as long as the momentary generated magnetic field at various locations in space is known. In a general setting, the magnetic field reading by a sensor 31 can be described as:

$$M_{RX}(t) = M_0 + R^t(t)B_0 + R^t(t)M(\vec{r}, t)$$

where $M(\vec{r}, t)$ is the known generated magnetic field in coordinates of the generator transmitter 20 at point $\vec{r}$ and time t. For example, $M(\vec{r}, t)$ can be modeled as the superposition of general sinusoidal electromagnetic coil fields with different frequencies, for example:

$$M(\vec{r}, t) = \sum_i B_i(\vec{r}) \sin(2\pi f_i t)$$

where $B_i(\vec{r})$ is the magnetic field due to the i-th electromagnetic coil and $f_i$ is the operating frequency of the i-th EM coil.

In some embodiments of the present disclosure, Kalman filter may be used to track a position and/or orientation state of sensor 31. By using Kalman filter algorithm, a faster refresh rate for updating the detected state of sensor 31 and better overall tracking performance may be obtained. It will be appreciated that in a low-frequency magnetometer-based localization system, in which the sampling rate of sensor 31 may be, for example, between 100 Hz-1000 Hz, the magnetic field frequency of transmitter 20 may be constrained to about 10-100 Hz. In this case, a localization algorithm which relies on the decomposition of full periods of the sine waves to field amplitudes, is doomed to have a slow refresh rate and inferior overall tracking performance, which is unacceptable for most medical applications. In some embodiments of the present disclosure, server 10 solves the problem of slow refresh rate by using a Kalman filter algorithm incorporated in its catheter localization algorithm, which may yield, in some embodiments, a refresh rate of at least 100 Hz, fast enough for most medical applications.

Server 10 may use a mathematical model to describe motion of catheter tube 36. In some embodiments, server 10 may track each sensor 31 independently. For example, server 10 may predict the state of sensor 31 of a next timeframe, for example based on the state in a current timeframe, and/or based on IMU sensor bundle measurements that may be used to correct the prediction. For example, a motion model may use a constant and/or damped velocity for a position and/or orientation of sensor 31. For example, server 10 may use for a Kalman filter algorithm a state vector for sensor 31. The state vector may be composed of parameters such as, for example, $M_0$, $B_0$, $\vec{r}$, $Q$, $\dot{\vec{r}}$, $\vec{\omega}$, which may be the sensor bias, environmental magnetic bias, position in coordinates of transmitter 20/20a, orientation in coordinates of transmitter 20/20a (expressed as a quaternion), velocity in coordinates of transmitter 20/20a, angular-velocity in local coordinates (not to be confused with the frequency of the transmitted magnetic field, also sometimes denoted by ω), respectively. $M_0$, $B_0$ may vary slow enough to be modeled as constant or nearly constant. Deviation from constant velocities, e.g. existence of linear and angular accelerations, and/or deviation from constant environmental magnetic field and sensor bias, can be modeled, for example, as process noise, with corresponding covariance matrices.

After defining the state vector and its dynamic model, server 10 may predict a state vector of sensor 31 and/or state covariance between consecutive timeframes. Then, the state vector may be corrected according to the prediction to yield a better fit to the newly obtained sensor magnetic field reading. For example, the tracked state vector, whose magnetic measurement is modeled as $M_{RX}^{(DUAL)}(t)$, may yield a vector which deviates from the latest sensed magnetic reading only by a small amount of random noise, whose standard deviation can be set according to its typical value, for example from a datasheet of the respective magnetometer.

In some embodiments, the motion model used by server 10 is modular and/or extendable. For example, with the presence of optional accelerometer or gyroscope sensors, for example in sensor 31, the Kalman filter can be extended to include an additional state for linear acceleration, $\ddot{\vec{r}}$. The accelerometer-gyroscope readings can be processed in an IMU-fusion filter to separate between gravitational acceleration and linear acceleration. The computed linear acceleration can then be fed into the Kalman filter as measurements for $\ddot{\vec{r}}$ when correcting the state vector, while the gyroscope readings can serve as measurements for $\vec{\omega}$. The extra accelerometer-gyroscope readings may significantly reduce the filter's latency and provide even higher-rate, more stable localization.

In another configuration, for example instead of separating between "classical" IMU-fusion orientation tracking and magnetometer-based 6DOF tracking, additional IMU data (accelerometer, gyroscope) can be combined with magnetometer readings in a single unified extended Kalman filter. The states of this filter may be: $M_0$, $B_0$, $\vec{r}$, $Q$, $\dot{\vec{r}}$, $\vec{\omega}$, $\ddot{\vec{r}}$ (as explained above). This unified filter may use a constant (or damped) acceleration model for its position. Each sensor 31

(magnetometer, optional accelerometer & gyroscope) may contribute a measurement for the "update" step, in which all measurements need to be explained using the filter's states. For example, magnetic measurements may be explained with $M_{RX}^{(DUAL)}$ using $M_0$, $B_0$, $\vec{r}$, $Q$, accelerometer measurements (which are a superposition between gravitational acceleration and linear acceleration) may be expressed by combining $Q$, $\ddot{\vec{r}}$, and gyroscope measurements can be explained directly by $\vec{\omega}$.

Using an extended Kalman filter for solving for 6DOF localization of sensors 31 and/or tube 36 can be easily generalized for any type of transmitter 20, not limited to the transmitter 20 described with reference to FIG. 2. As long as each magnetic measurement can be explained using the states of the filter, the filter may be fully functional and provide fast 6DOF solutions. This is an excellent property of the extended Kalman filter, where all is needed for high-quality solutions of the states is to be able to model the measurements using those states.

For example, in case of using an electromagnetic generator transmitter 20 that generates magnetic field by electromagnetic coils, $M_{RX}^{(DUAL)}(t)$ may be replaced with the more general formula:

$$M_{RX}(t)=M_0+R^t(t)B_0+R^t(t)M(\vec{r},t)$$

Where $M(\vec{r}, t)$ depends on the magnetic field generated by the transmitter 20 being used. This makes the use of an extended Kalman filter for a 6DOF localization solution of sensors 31/tube 36 invariant to the choice of transmitter, which is extremely powerful and flexible for many general purposes.

According to some embodiments of the present disclosure, server 10 may use in its catheter localization algorithm known structural relationships between sensors 31 to calculate an estimation of the position, orientation and/or curve of tube 36 as a whole, for example rather than calculating position and/or orientation for each of sensors 31 separately.

Figure 4:
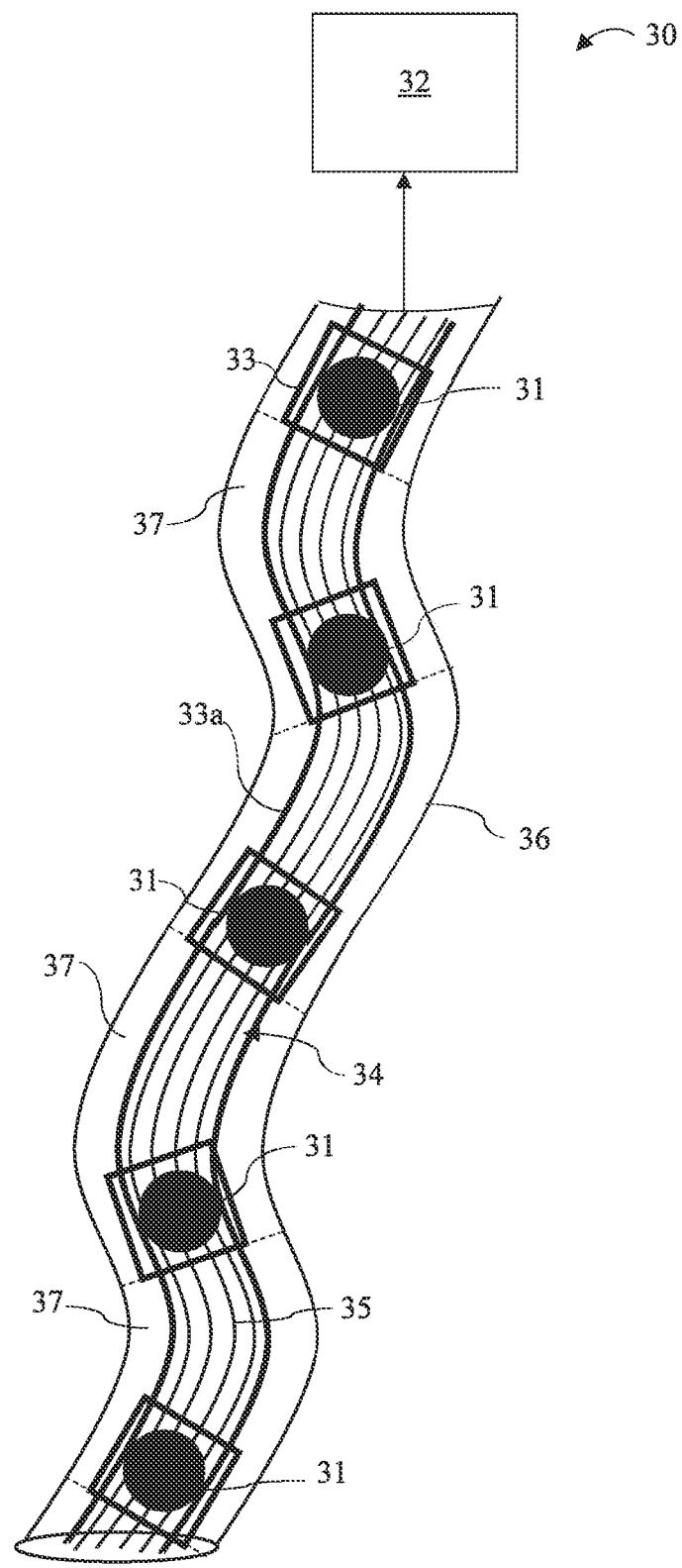
FIG. 4 is a schematic illustration of a catheter according to some embodiments of the present disclosure.

Reference is now made to FIG. 4, which is a schematic illustration of catheter 30, according to some embodiments of the present disclosure. Catheter 30 may include a flexible PCB 33 within and/or placed along catheter tube 36. PCB 33 may be communicationally connected to microcontroller 32, for example by the same data bus 34 that may include few wire lines 35, for example two to four wires 35. For example, inter-integrated circuit (I2C) is used as a digital connection interface between microcontroller 32 and sensors 31 installed along PCB 33. In some embodiments, it only requires two wires 35 for exchange of data between the sensors and microcontroller 32, which may be beneficial for a small catheter where wire count should be kept small.

In exemplary configurations, flexible PCB 33 may have eight, five, ten, or any suitable number of sensors 31 installed thereon, for example all connected to the same I2C bus (for example serial data and serial clock lines). In some embodiments, microcontroller 32 is connected to flexible PCB 33 using a 4-wires shielded cable, for example including voltage and/or ground wires. Microcontroller 32 may provide the voltage and/or ground for digital sensors 31, for example additionally to two data lines for the readings of digital measurements by sensors 31. Microcontroller 32 may read sensors 31, for example, sequentially and send the sensor readings to server 10, for example over wired and/or wireless communication. In a slightly different configuration, five wires 35 may be used to connect between microcontroller 32 and flexible PCB 33 and/or sensors 31. For example, additional data line(s) may be added. For example, some of sensors 31 may use a first data line wire, and other sensors 31 may use a second data line wire. Accordingly, for example, microcontroller 32 may sample and/or read some of sensors 31, simultaneously, thus, for example, reducing the overall I2C sampling time. For example, in case of two parallel data line wires, the sampling time may be reduced by half.

The design of flexible PCB 33 and/or positioning of sensors 31 thereon may provide the positions and/or orientations of sensors 31, for example, when PCB 33 is straight. For example, during the manufacturing process, PCB 33, may be attached inside and/or along tube 36, for example in a manner that determines the positions and/or orientations of sensors 31, for example, with respect to tube 36. Server 10 may be calibrated to provide to server 10 the initial 6DOF orientation and/or position of sensor 31, for example 6DOF orientation and/or position of sensor 31 when tube 36 is straight. The initial 6DOF orientation and/or position data, along with information about rigidity and/or flexibility limitations of tube 36, may be incorporated in the catheter localization algorithm as shape constraints. For example, based on incorporated shape constraints, two neighboring sensors 31 cannot point to opposite directions.

This way, a more sophisticated localization algorithm, which takes shape constraints into account, can enable system 100 to be both compact and robust. Solving for the 6DOF position and/or orientation of all sensors 31 while imposing physical shape constraints on catheter tube 36 full-curve shape may essentially reduce the number of parameters of the motion model and thus, for example, may prevent over-fitting of the measured data. By using the shape constraints, server 10 may refrain from erroneously calculating a position and/or orientation of sensor 31 due to a noisy or distorted measurement, because the position and/or orientation solution must comply, for example, with position and/or orientation solutions of neighboring sensors 31, for example so they would together describe a smooth, physically plausible catheter tube 36.

A common challenge in electromagnetic localization systems is to be as accurate as possible in the presence of magnetic distortion. For low frequency systems, the main distorters are objects made of ferromagnetic materials. In the hospital settings, these may be found in the frame of the patient's bed, or as part of the instruments used by physicians (e.g. surgical tools) during a medical procedure. When a localization system does not take magnetic distortion into account, it may be extremely inaccurate (position errors >1 cm) and may be unfit for medical use. Magnetic distorters can be divided to static distorters whose position relative to the system can be fixed, and dynamic distorters which can move between medical procedures and/or during a procedure. Static magnetic distorters are objects that can be fixed relative to the magnetic field generator during the deployment of a localization system, and will stay permanently fixed during the lifetime use of the localization system. In some embodiments of the present disclosure, static distortion can be addressed by a process of magnetic mapping, where the magnetic fields in the sensing radius around transmitter(s) 20 are no longer assumed to be perfect dipole fields, but are rather "mapped" in an offline process with calibrated sensors 31 and are later used by the real-time solver in order to solve for accurate 6DOF position and orientation even under the distorted fields. In some embodiments, server 10 may take into account dynamic distortion by incorporating the distortion in the localization algorithm, for example in order to provide accurate solutions.

Different methods can be used to compensate for dynamic magnetic distortions. One method would be to incorporate physical distortion model inside the model of the sensed magnetic field of sensor 31. This addition of parameters may yield less robust solutions if each sensor 31 is solved independently, due to the solver's ability to over-fit the 6DOF and distortion model parameters to the measured sensor 31 data, even in case of more than one transmitter 20. For this reason, the solver should be constrained to parameters that make "mechanical sense", both in terms of the solved geometry of the sensors 31 in the catheter tube 36 and the geometrical properties of the distortion field. Another way of addressing dynamic distortion may include imposing shape constraints on catheter tube 36 full-curve shape. The 6DOF orientation and position solution calculated by server 10 may not deviate much from the actual position and orientation of sensor 31 along the curve of tube 36, for example because they are regularized by shape constraints, as described above. While dynamic distortion is usually a local artifact that deforms position and orientation calculations quite differently, the imposed shape constraints will make sure that the multiple sensor 31 position and/or orientation solutions would still make sense in terms of the catheter tube 36 fully solved curve. The undesirable effect of distortion will then be naturally reduced just due to the imposed shape constraints.

There are several methods for imposing shape constraints in the localization algorithm. One option would be to approximate the catheter's shape as a set of line segments 37, with a single sensor 31 at the end of each segment 37. The orientation of each sensor 31 with respect to its surrounding catheter and its distance to its adjacent receivers are assumed to be fixed and known, for example by calibration of the localization algorithm. Hence, according to some embodiments of the present disclosure, the entire catheter curve can be modeled by a single set of 6DOF that may belong to the one of the sensors 31, for example a first sensor 31 along tube 36, for example the closest in the communication path to server 10 and/or to microcontroller 32, and for each sensor 31 two spherical angles which correspond to the bend of the catheter in segment 37 between the sensor 31 and a preceding, for example neighboring, sensor 31, and/or an additional angle to represent the internal twist of tube 36 in the corresponding line segment 37. In some embodiments of the present invention, PCB 33 includes thinner portions 33a, for example in between sensors 31, that are thinner, for example, from portions of PCB 33 where sensors 31 are located, for example in order to facilitate enhances flexibility and/or bendability of PCB 33 in portions 33a.

Figure 5:
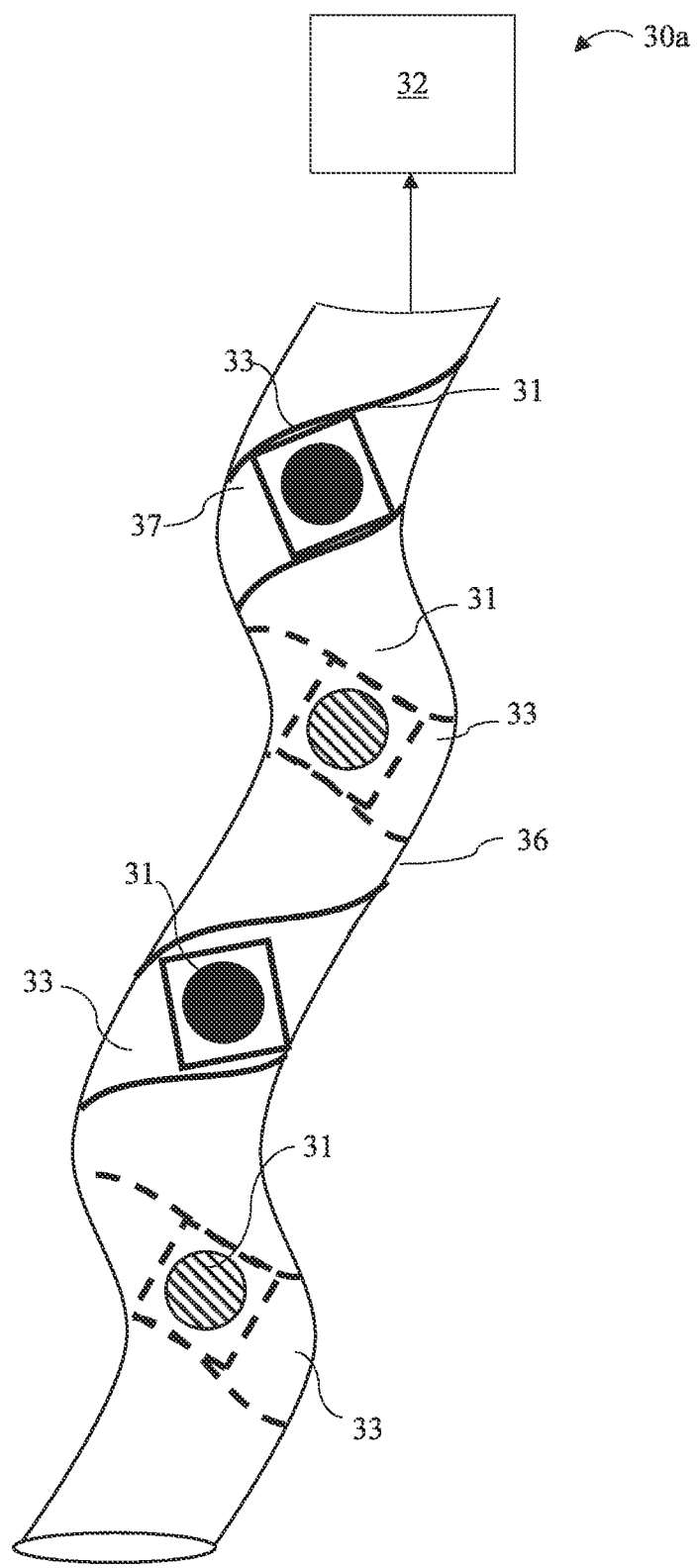
FIG. 5 is a schematic illustration of a catheter device, according to some other embodiments of the present disclosure.

Reference is now made to FIG. 5, which is a schematic illustration of a catheter 30a, according to some embodiments of the present disclosure. In some embodiments, flexible PCB 33 is wrapped in a helix manner on and/or along an inner or outer wall of tube 36, as shown in FIG. 5, for example in order to facilitate enhances flexibility and/or bendability of catheter 30a, e.g. of tube 36 together with PCB 33. As described in more detail herein, for example with reference to FIG. 6, PCB 33 may carry, for example further to sensors 31 and/or data bus 34, a plurality of dipole magnets.

Accordingly, in some embodiments, the number of parameters in the catheter's shape is significantly reduced from 6DOF orientation and position for each sensor 31 to 6DOF orientation and position for a first sensor 31 plus three angles for each additional sensor 31. In this method, the solved orientation and position of sensors 31 are less prone to over-fitting, for example due to hard constraints which assume a fixed distance between sensors 31, and, for example a fixed orientation of each sensor 31 with respect to a certain surrounding segment of tube 36. An alternative is to use a soft model, in which the position and orientation of sensor 31 with respect to a previous, for example neighboring, sensor 31, are parameterized with regularization terms to penalize the parameters, for example:

$$E_{dist} = (\|r_{i+1} - r_i\| - D_i^{(cal)})^2$$

Where: $r_i$, $r_{i+1}$—positions of two sequential sensors 31, respectively, and $D_i^{(cal)}$—the calibrated distances between the two sequential sensors 31. Alternatively, an inequality can be used to constrain the solved distance to a certain range, e.g.: $0.9 D_i^{(cal)} \leq \|r_{i+1} - r_i\| \leq 1.1 D_i^{(cal)}$. Such a model, which takes the parameters of sensors 31 into account, can be formalized in a single Extended Kalman Filter.

Another possible method is to solve orientation and/or position for sensor 31, for example with an independent solver, may include fitting of a mechanical model to the curve of catheter tube 36 in segments 37 between sensors 31, and then force an individual sensor 31 to lie as close as possible to its relevant position and orientation along the curve of tube 36. This could be accomplished, for example, by fitting a low degree polynomial between solved positions of sensors 31, and then use the model's positions of sensors 31 as (noisy) position measurements to the independent solvers. Another more general way to achieve this is by describing the curve of tube 36 as a general curve with some energy function, which may encode the catheter's shape constraints (for example, position and orientation smoothness constraints, distance along the curve between sequential sensors etc.). The curve of tube 36 can then be fitted to the noisy or distorted measurements of sensors 31 by means of non-linear optimization, minimizing errors of sensors 31 and the energy function of the curve of tube 36, simultaneously. The method of alternating between individual sensor 31 localization computations and full-curve fitting computations may be beneficial, because it may allow the computations to be executed in parallel. Instead of solving the full-curve shape of tube 36 as a whole inside a potentially gigantic Extended Kalman filter, the task may be broken into smaller subtasks, such as solving localization of each sensor 31 individually, and the sub-results may then be glued together in the form of the final catheter's curve fitting.

In some embodiments, it is further possible to reduce the system's number of degrees of freedom by assuming that the environmental magnetic field (e.g. Earth's magnetic field) is uniform along the curve of the catheter. The solved environmental magnetic field is denoted above by $B_0$ and is solved for each sensor of the catheter independently (in transmitter's coordinate system). By assuming that the environmental magnetic field is uniform along the catheter, $B_0$ can be jointly solved for all sensors of the catheter, thus reducing the degrees of freedom of the system and decreasing the risk of over-fitting. Intuitively, sharing $B_0$ between sensors imposes constraints on the relative orientations between sensors (which together with full catheter shape-constraints, also imposes constraints on the relative positions of the sensors). Assuming that $B_0$ is uniform along the entire catheter might not be correct in cases where magnetic distortion is present; in these cases the environmental magnetic field deforms and may vary slowly in space, and in particular along the catheter curve. In this case, a softer assumption may be utilized, assuming that $B_0$ is almost constant between neighboring sensors. This soft assumption can be expressed as an energy function and minimized in least squares sense (as part of the full catheter solver optimization): $E_{env}=\Sigma_i\|B_0^i-B_0^{i+1}\|^2$, it requires the solved environmental magnetic fields of neighboring sensors ($B_0^i$, $B_0^{i+1}$) to be similar to each other. In all cases mentioned above, the solved $B_0$ are no longer independent per-sensor, but rather tied together in order to pose some constraints on the in-between orientation of the sensors along the catheter.

In another embodiment, instead of just using the natural environmental magnetic field (e.g. Earth's) for imposing constraints on the solved 6DOF of the sensors, artificial constant magnetic fields can be created by incorporating small magnets along the catheter's curve. With the magnets placed at known positions and directions, $B_0$ can be fully predicted for any given configuration of the full catheter curve. $B_0$ may also depend on the relative positions and orientations of the sensors (which by shape smoothness constraints also uniquely define the relative positions and orientations of the incorporated magnets), since each such different configuration can potentially cast other DC magnetic fields (e.g. magnetic fields with substantially zero frequency) on each sensor along the curve by the differently positioned and oriented incorporated small magnets. By knowing the exact position and orientation of each incorporated magnet for each full curve configuration, $B_0$ of each sensor can be predicted so that system's number of degrees of freedom may further decrease.

Figure 6:
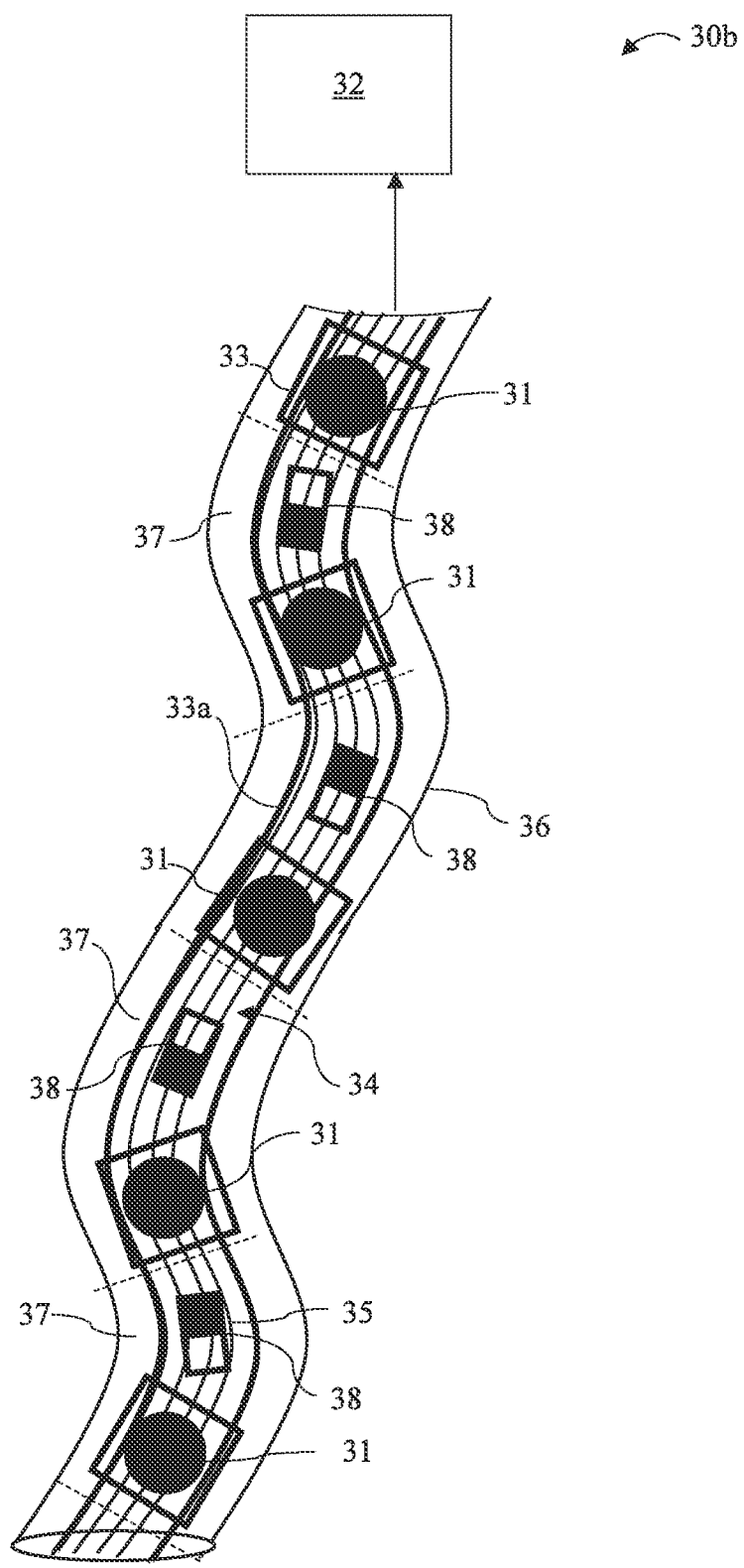
FIG. 6 is a schematic illustration of a catheter device, according to some other embodiments of the present disclosure.

Reference is now made to FIG. 6, which is a schematic illustration of a catheter 30b, according to some embodiments of the present disclosure. Catheter 30a may include a plurality of dipole magnets 38 which are positioned between the sensors, for example in equal distances. For example, dipole magnets 38 are oriented so that two magnets 38 located at two sides of a sensor 31 have opposite dipole directions, when tube 36 is in a straight state. When catheter tube 36 is straight, each sensor may sense the superposition of perfectly aligned positive and negative dipole fields so the contribution of two magnets located at two sides of sensor 31 may be canceled, and thus, for example, the $B_0$ sensed by sensor 31 may substantially include only Earth's magnetic field. When the catheter starts to bend the contribution of two magnets located at two sides of sensor 31 may grow linearly as $C \sin(\alpha)$, wherein $\alpha$ is the angle of bend and $C$ is some known constant depending on the relative positions and strength of magnets 38. In this example, it is evident how $B_0$ encodes more information about the relative orientations between neighboring sensors. By incorporating magnets 38 along the catheter, as in this example, more efficient constraints may be achieved on the relative sensor orientations than in the case of just using Earth's magnetic field, in terms of SNR (by incorporating relatively strong magnets), reliability (the incorporated magnets are much less prone to magnetic distortion) and geometry (posing the magnets in carefully chosen orientations tunes the constraints as desired for a specific application).

In some embodiments of the present invention, system 100 may be used for organ deformation tracking in minimally invasive surgery. For example, a full-curve catheter localization is used in order to track the deformation which is applied to an internal organ by some external means. For example, during a laparoscopic procedure, organs may be manipulated using tools to the extent where it is hard to tell which part of the organ is visible in the live laparoscopic video. For that reason, visual markers are sometimes utilized; at the beginning of the procedure, and before applying any manipulation to the organ, markers are placed on the surface of the organ at known anatomical landmarks. They are then visually tracked throughout the procedure and used as registration fiducials in order to enable some sort of anatomical localization, even though the organ may be highly manipulated and deformed compared to its initial known state.

Unfortunately, in some procedures such as lung laparoscopy, where localization is critical for identifying hidden blood vessels, the surface of the lungs does not contain enough visual information for placing anatomical markers (i.e., markers whose positions in the anatomy are well known). Furthermore, due to the lung's highly flexible form, tracking anatomical features on the surface of the lung does not necessarily extend well for the tracking of important anatomical features inside the lung, such as airways and blood-vessels; the surface does not necessarily predicts well the internal state of the lung. Finally, visual markers and optical tracking systems are prone to occlusions, motion blur, three-dimensional from two-dimensional computational problems and other ills which make most optical-based systems unfit for the purpose of highly accurate laparoscopic guidance.

The newly invented full-curve flex catheter tracking can address the flexible registration problem quite easily: In a preoperative stage, one or more flex-track catheters are inserted into known airways using a bronchoscope. Each catheter stays stationary relative to anatomy (as described below) and provides full-curve localization for an airway which is close to some region of interest (ROI). All important anatomical features in some ROI can then be displayed in real-time by employing real-time registration between the fully tracked catheter and a preoperative CT scan. During the laparoscopic procedure, the catheter (or multiple catheters) is bent and twisted, but still holds its anatomical position inside some known airway. The catheter (or multiple catheters) can then serve as a skeleton for the lung, which is fully tracked in real-time, and can provide for a smooth, real-time flexible registration between important anatomical features taken from preoperative CT and the real-time deformed lung. By placing an additional sensor on the laparoscopic camera, those anatomical features can be displayed as an overlay on the live laparoscopic video, thus provide guidance for laparoscopic procedures in the lungs, which is fully real-time and flexible by its nature.

In order for the catheter to hold still relative to the anatomy, specifically in organs containing tubes (blood vessels or airways), it should be attached to the anatomical tube. Attachment should be made at the distal allowing the catheter to track organ from the distal point of the catheter and allowing the organ to stretch or shrink freely. Attachment can be achieved using a balloon or hooks, or by friction with the tissue. In order for the catheter to comply with anatomy without deforming it the catheter needs to be highly flexible. Flexibility is achieved by using flexible plastic tubing in the construction of the catheter shaft. It is also important to reduce the rigidity of the flexible PCB. The rigidity of the flexible PCB material is derived from the polyimide stiffness, the number of PCB layers and amount of copper used. The increase in flexibility can be achieved by PCB geometrical design, for example by reducing the width of PCB 33 between sensors 31, and/or routing the conductors in tortuous way and cutting PCB 33 parallel to the tortuous path to reduce rotational rigidity.

In some embodiments of the present invention, system 100 may be used for electromagnetic navigation bronchoscopy (ENB). A full-curve real-time localized catheter has great advantages in terms of registration accuracies within an ENB procedure. Instead of relying on past samples of the catheter's tip alone, which are very "noisy" due to breathing and heart movement, the full catheter is always visible in the system and can be used as a whole for registration between the coordinates of transmitter 20 and the airways map. The catheter's very specific bend and shape inside the airways may teach the system about the most probable location of the catheter, as a full curve, inside the airways. Its shape can be matched to the map and be used as a unique signature for its anatomical location inside the airways. For initial registration, the full-curve localization provides many more samples during an unsupervised survey in the lungs compared to just the catheter's tip—full paths may be drawn in coordinates of transmitter 20 and can be matched to the map in an unsupervised fashion, thus improving the registration's stability and accuracy. For adaptive registration, the fully localized catheter's curve can be matched into airways inside some region of interest (ROI) until the most probable airway is found. This accommodates better for breathing and changes in body posture; the full-curve localization is immediate, unlike history-based approaches in which the accumulated samples inside the time window may undergo different deformation over time (for example, if they were taken during different phases of breathing). Another form of adaptive registration is also possible, where the full-curve localization can be used as a skeletonization of the lungs and serve as the basic ingredient for a flexible deformable lung model. By analyzing the full curve of the catheter one may understand how certain major airways, through which the catheter passes, are deformed, then conclude how surrounding areas are deformed by using some extrapolation model.

Furthermore, catheter steering may become easier: it's not uncommon for a physician to experience difficulties while trying to perform a sharp turn with a catheter inside the lungs. The physician would then try over and over again to pull, rotate and push the catheter based on the single-sensor feedback which they receive from the system. With a full-curve localization the physician can see the full bend of the catheter and have a better understanding of how the applied forces translate into distal catheter movement under the stress of the surrounding tissues. Based on this much more informative feedback, he can then generate more precise steering gestures which would translate into the exact desired distal motion with much less trial and error.

In addition, full-curve localization is much easier to register with other modalities such as fluoroscopy. During fluoroscopy the full length of the catheter is visible in the X-ray image due to the radio-opacity of the catheter. In traditional EM localization systems only the tip is visible. In such situation, it would be difficult for a physician to match between the fluoroscopic image and the image displayed by the localization system. With full catheter localization both the catheter's full length is visible both in the fluoroscopic image as well as the magnetic localization system, which makes it much easier for a physician to match between the different modalities.

In some embodiments of the present disclosure, system 100 may be used for electromagnetic guided colonoscopy where full catheter localization proves to be beneficial.

It will be appreciated that some embodiments of the present invention are applicable to any elongated flexible body and not only to a catheter, with the required changes.

Some embodiments of the present disclosure may include a system, a method, and/or a computer program product. The computer program product may include a tangible non-transitory computer readable storage medium (or media) having computer readable program instructions thereon for causing a processor to carry out aspects of the present disclosure. Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including any object-oriented programming language and/or conventional procedural programming languages.

In the context of some embodiments of the present disclosure, by way of example and without limiting, terms such as 'operating' or 'executing' imply also capabilities, such as 'operable' or 'executable', respectively.

Conjugated terms such as, by way of example, 'a thing property' implies a property of the thing, unless otherwise clearly evident from the context thereof.

The terms 'processor' or 'computer', or system thereof, are used herein as ordinary context of the art, such as a general purpose processor, or a portable device such as a smart phone or a tablet computer, or a micro-processor, or a RISC processor, or a DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

The terms 'software', 'program', 'software procedure' or 'procedure' or 'software code' or 'code' or 'application' may be used interchangeably according to the context thereof, and denote one or more instructions or directives or electronic circuitry for performing a sequence of operations that generally represent an algorithm and/or other process or method. The program is stored in or on a medium such as RAM, ROM, or disk, or embedded in a circuitry accessible and executable by an apparatus such as a processor or other circuitry. The processor and program may constitute the same apparatus, at least partially, such as an array of electronic gates, such as FPGA or ASIC, designed to perform a programmed sequence of operations, optionally comprising or linked with a processor or other circuitry.

The term 'configuring' and/or 'adapting' for an objective, or a variation thereof, implies using at least a software and/or electronic circuit and/or auxiliary apparatus designed and/or implemented and/or operable or operative to achieve the objective.

A device storing and/or comprising a program and/or data constitutes an article of manufacture. Unless otherwise specified, the program and/or data are stored in or on a non-transitory medium.

In case electrical or electronic equipment is disclosed it is assumed that an appropriate power supply is used for the operation thereof.

The flowchart and block diagrams illustrate architecture, functionality or an operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function(s). It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

What is claimed is:

1. A method for magnetic tracking of a flexible device, which is a flexible catheter device or another flexible elongated device, said flexible device comprising a tip and a body, the method comprising:
   a. receiving by a host server a plurality of sensed values of a local magnetic field, sensed by a respective plurality of digital magnetometers, the digital magnetometers are located along said flexible device, on at least one of said tip and said body of said flexible device, wherein the sensed values are at least partially due to at least one alternating magnetic field generated by at least one magnetic field generator; and
   b. calculating by the host server, based on the sensed magnetic field values and source amplitude and frequency of each generated magnetic field, a localization of said flexible device;
   wherein said calculating comprises calculating for each digital magnetometer from said plurality of digital magnetometers a three-dimensional position and orientation in relation to said alternating magnetic field;
   wherein a plurality of said digital magnetometers are located on a same digital communication bus.

2. The method of claim 1, wherein the host server is included in a controller of the digital magnetometers.

3. The method of claim 1, comprising:
   a. receiving by a host server, from at least one generator of an alternating magnetic field, a momentary phase value of the generated magnetic field; wherein phase data is received from the at least one generator in full rate of a magnetometer located at the at least one generator;
   b. associating by the host server between the momentary phase value and at least some of the sensed magnetic field values received from the digital magnetometers; wherein the associating is based on a corresponding clock reading shared among the magnetic field generator, a controller of the digital magnetometers and the host server; and wherein the clock reading is shared by the magnetic field generator or by a clock source shared among the field generator, a controller of the digital magnetometers and the host server; and
   c. calculating by the host server, based on the magnetic field values and the associated phase value, a localization of the flexible device.

4. The method of claim 1, wherein the calculation incorporates known structural relationships between the digital magnetometers to calculate an estimation of the position, orientation or curve of the flexible device as a whole.

5. The method of claim 1, wherein the sensed values are at least partially due to at least two generated magnetic fields generated by at least two corresponding generators, wherein the at least two generators share the same clock or have synchronized clocks or share a clock source.

6. The method of claim 5, wherein the at least two generated magnetic fields operate at different frequencies.

7. The method of claim 1, wherein said calculating comprises imposing a shape constraints of said flexible device on said calculating of said localization of said flexible device.

8. The method of claim 1, wherein said host server is included in a controller in said flexible catheter device.

9. The method of claim 1, wherein said digital magnetometers are digital DC magnetometers.

10. The method of claim 1, wherein said frequency is lower than 500 Hz.

11. The method of claim 1, wherein said frequency is from about 10 Hz to about 100 Hz.

12. A system for magnetic tracking of a flexible device, which is a flexible catheter device or another flexible elongated device, the system comprising:
   a. at least one generator, each configured to generate an alternating magnetic field;
   b. a flexible device comprising:
      i. a tip and a body;
      ii. a plurality of digital magnetometers, the digital magnetometers are located along said flexible device, on at least one of said tip and said body of said flexible device, each configured to communicate sensed values of a local magnetic field, wherein the sensed values are at least partially due to the generated magnetic field; and
   c. a host server configured to:
      iii. receive the sensed local magnetic field values from the corresponding digital magnetometers; and
      iv. calculate, based on the magnetic field values and the source amplitude and frequency, a localization of said flexible device;
   wherein said calculate comprises calculating for each digital magnetometer from said plurality of digital magnetometers a three-dimensional position and orientation in relation to said alternating magnetic field;
   wherein a plurality of said digital magnetometers are located on a same digital communication bus.

13. The system of claim 12, wherein the host server is included in a controller of the digital magnetometers.

14. The system of claim 12, wherein the host server is configured to:
   a. receive, from at least one generator of an alternating magnetic field, a momentary phase value of the generated magnetic field;
   b. associate by the host server between the momentary phase value and at least some of the sensed magnetic field values received from the digital magnetometers; wherein the associating is based on a corresponding clock source reading shared among the magnetic field generator, a controller of the digital magnetometers and the host server; and c. calculate by the host server, based on the magnetic field values and the associated phase value, a localization of the flexible device.

15. The system of claim 12, wherein the device further comprises a flexible PCB along the flexible device, wherein the digital magnetometers are located along the flexible PCB.

16. The system of claim 15, wherein the flexible PCB is wrapped in a helix manner on a wall of the flexible device.

17. The system of claim 12, wherein the device further comprises a communication bus configured to carry the sensed values data digitally from the plurality of digital magnetometers towards the server.

18. The system of claim 17, wherein the communication bus includes up to four wire lines that may carry the sensed values digital data from and provide power to the plurality of digital magnetometers.

19. The system of claim 12, wherein the at least one generator comprises one or more of:

a. an internal clock and is configured to share its clock readings with the digital magnetometers and with the host server; and b. a magnetometer configured to detect phase data.

20. The system of claim 12, wherein the system includes at least two generators that generate at least two respective magnetic fields that may operate at different frequencies, wherein the at least two generators share the same clock or have synchronized clocks or share a clock source.

21. The system of claim 12, wherein the at least one generator comprises at least one permanent magnet and a motor device that rotates the magnet in a determined frequency.

22. The system of claim 12, wherein the at least one generator comprises one or more transmitting coils which generate EM fields of different geometry.

23. The system of claim 12, wherein the device includes a plurality of dipole magnets positioned between the digital magnetometers.

24. The system of claim 12, wherein the flexible catheter device is wireless.

25. The system of claim 12, wherein said calculate comprises imposing a shape constraints of said flexible device on said calculated localization of said flexible device.

26. The system of claim 12, wherein said host server is included in a controller in said flexible catheter device.

27. The system of claim 12, wherein said digital magnetometers are digital DC magnetometers.

28. The system of claim 12, wherein said frequency is lower than 500 Hz.

29. The system of claim 12, wherein said frequency is from about 10 Hz to about 100 Hz.

30. The system of claim 12, wherein said flexible device comprises a plurality of digital IMU sensors.

31. The system of claim 30, wherein said plurality of digital IMU sensors are located on said tip and along said body of said flexible device.

32. The system of claim 30, wherein a plurality of said digital IMU sensors are located on a same digital communication bus.

33. The system of claim 30, wherein said plurality of digital IMU sensors are placed in predefined locations along said flexible device.

34. The system of claim 30, wherein said plurality of digital IMU sensors are placed at predefined distances between them along said flexible device.

35. The method of claim 1, wherein said flexible device comprises a plurality of digital IMU sensors.

36. The method of claim 35, wherein said plurality of digital IMU sensors are located on said tip and along said body of said flexible device.

37. The method of claim 35, wherein a plurality of said digital IMU sensors are located on a same digital communication bus.

38. The method of claim 35, wherein said plurality of digital IMU sensors are placed in predefined locations along said flexible device.

39. The method of claim 35, wherein said plurality of digital IMU sensors are placed at predefined distances between them along said flexible device.

40. The method of claim 1, wherein, said source amplitude and said frequency of each generated magnetic field are given to said host server.

41. The system of claim 12, wherein, said source amplitude and said frequency of each generated magnetic field are given to said host server.

42. The method of claim 1, wherein said method further comprises calculating an estimation of a full-curve localization of said flexible device along its length.

43. The system of claim 12, wherein said host is further configured to calculate an estimation of a full-curve localization of said flexible device along its length.

* * * * *